United States Patent [19]

Murray et al.

[11] 4,450,356
[45] May 22, 1984

[54] FREQUENCY-MIXED $CO_2$ LASER RADAR FOR REMOTE DETECTION OF GASES IN THE ATMOSPHERE

[75] Inventors: Edward R. Murray; Jan E. van der Laan, both of Palo Alto; Arne Rosengreen, Los Altos; Robert L. Byer, Stanford, all of Calif.

[73] Assignee: SRI International, Menlo Park, Calif.

[21] Appl. No.: 385,490

[22] Filed: Jun. 7, 1982

[51] Int. Cl.³ .................................. G01N 21/39
[52] U.S. Cl. ................................. 250/339; 356/437
[58] Field of Search ............... 250/339, 573, 574, 338, 250/343, 345, 346, 372, 373; 356/437, 438, 439, 409, 342

[56] References Cited

FOREIGN PATENT DOCUMENTS 2389888  1/1979  France .............................. 356/437

OTHER PUBLICATIONS

Stewart, "Development of a Pulsed 9.5 μm Lidar for Regional Scale $O_3$ Measurement", Opt. Eng., 19 (4), Jul./Aug. 1980, pp. 503–507.
Browell, "Airborne Differential Absorption Lidar System for Water Vapor Investigations", Opt. Eng., 20 (1), Jan./Feb. 1981, pp. 84–90.
Murray, "Remote Measurement of Gases Using Differential-Absorption Lidar", Opt. Eng., 17 (1), Jan.-/Feb. 1978, pp. 30–38.

Primary Examiner—Alfred E. Smith
Assistant Examiner—Carolyn E. Fields
Attorney, Agent, or Firm—John P. Taylor

[57] ABSTRACT

Gases in the atmosphere are detected remotely using a frequency-mixed $CO_2$ laser beam formed by passing the beam from a first $CO_2$ laser through a frequency doubler and then frequency-adding the output to the frequency from a second $CO_2$ laser to obtain wavelengths in the 3 micron region. A first wavelength in this region, preselected for nonabsorption by the gases to be detected, is transmitted through the gases toward an object capable of reflecting the beam back. A second wavelength preselected as highly absorbed by the gases to be detected is then transmitted. The presence and quantity of the gases is then determined by the difference in the amount respectively absorbed at the two wavelengths.

10 Claims, 2 Drawing Figures

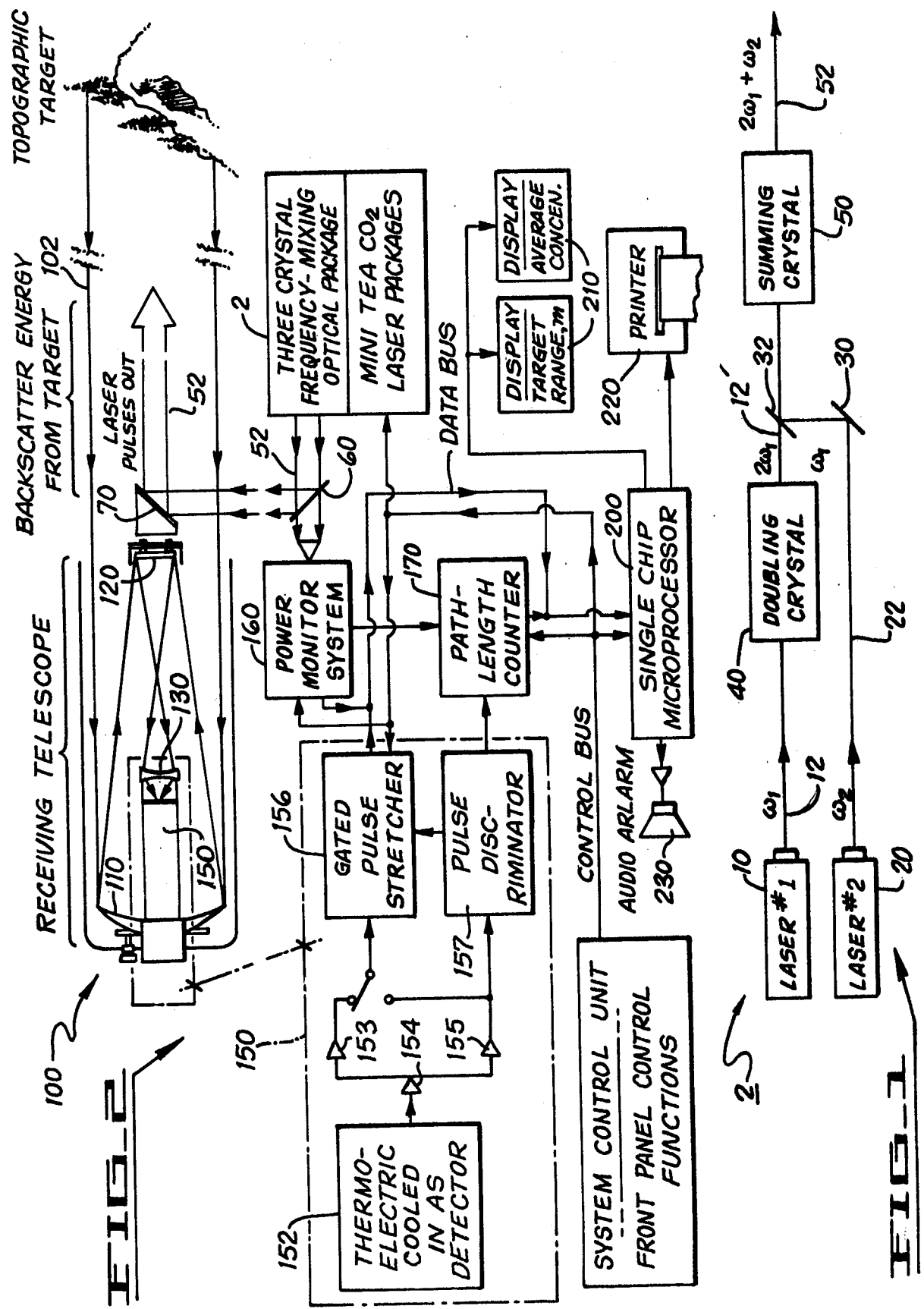

FREQUENCY-MIXED CO₂ LASER RADAR FOR REMOTE DETECTION OF GASES IN THE ATMOSPHERE

BACKGROUND OF THE INVENTION

This invention relates to the detection of gases using laser beams. More particularly this invention relates to the remote detecting of gases in the atmosphere using frequency-mixed radiation from $CO_2$ lasers.

The detection of gases in the atmosphere using laser beams in the infared region is known to those skilled in the art. Canadian Patent No. 808,760 describes the detection of hydrocarbon gases using noble gas lasers such as a helium-neon laser mounted in an aircraft. Briefly, the method comprises the use of two laser beams of slightly different wavelengths, either from the same laser or two lasers. One preselected wavelength is highly absorbed by the gas to be detected while the other is not thereby providing a differential coefficient. The laser beams pass through the gas in question and are reflected back to a common detection source which measures the intensity of the two beams. Any difference in the measured intensities determines the presence and quantity of the gas in question. Dust, water droplets and other light scattering materials in the atmosphere act in similar manner on the two beams and, thus, are factored out.

While such a detection scheme should be highly satisfactory in determining the presence or absence of preselected gases, in practice it is not, due to the restrictive number of wavelengths emitted by such lasers and the number of interfering gases possibly present in the atmosphere either singly or in combination. For example, the most popular and frequently used of such lasers, the helium-neon laser, only emits at 10 possible wavelengths. While these particular wavelengths, for example, have been found to be selective with respect to methane, they are not useful for detection of ethane.

Other laser beams may be substituted for the helium-neon laser to permit selective detection of other gases such as ethylene which cannot be detected satisfactorily with the helium-neon laser. Two of the present inventors published an article entitled "Remote Measurement of Ethylene Using a $CO_2$ Differential-Absorption Lidar" by E. R. Murray and J. E. van der Laan in Applied Optics, Volume 17 at page 814 (Mar. 1, 1978). This article describes the detection of ethylene gas in the atmosphere by selective absorption of wavelengths emitted by a $CO_2$ laser.

It is also known that the number of wavelengths emitted by a laser source can be increased as well as the frequency range changed by the use of doubling and mixing crystals. N. Menyuk and G. W. Iseler in an article entitled "Efficient Frequency Tripling of $CO_2$ -Laser Radiation in Tandem $CdGeAs_2$ Crystals" in Optics Letters, Volume 4, page 55 (Feb., 1979) describe frequency tripling of $CO_2$-laser radiation using $CdGeAs_2$ crystals to produce second-harmonic generation in one crystal followed by sum mixing of the fundamental and second harmonic in a second crystal.

However, in the use and application of such technologies for the detection of gases in the atmosphere wherein a number of different gases or mixtures may be present, the need still remains for a system capable of more flexibility. For example, the $CO_2$ laser systems in use emit radiation at 80 different wavelengths in the 10 micron region. While frequency tripling techniques will provide 80 wave-lengths in the 3 micron region, a region that is more usable in detection systems due to the lower attentuation, the number of wavelengths available is still too small to provide a useful spectral match with some gases. One needs a spectral pair for each gas to be detected. Furthermore it is often necessary to have more than one pair since some pairs may not be useful if other gases are also present. This is because some of these gases may intefere by having differential absorption coefficients at a particular pair of wavelengths that are sufficiently large so that it is impossible to distinguish these gases from each other. Thus it is desirable to have a large number of wavelengths available. For example, detection of methane by itself presents no problem. However, the difficulties can arise if one is attempting to measure methane in the presence of a number of other gases, as might be true when searching for a natural gas leak with various hydrocarbons emanating from the same source. Another example is petroleum exploration in which various other gases, both hydrocarbons and air pollutants, are potential interferants. It would, therefore, be highly desirable to have a system having available many more wavelengths from which to select wavelength pairs for analysis of a multitude of gases present either singly or in combination.

SUMMARY OF THE INVENTION

It has now been discovered that differential-absorption lidar can be used to detect a number of gases in the atmosphere by passing a $CO_2$ laser beam from a first $CO_2$ laser source through a frequency doubling crystal and then summing it with the output of a second $CO_2$ laser source. The resultant system is capable of producing as many as 6400 different wavelengths in the 3 micron region where numerous gases including light hydrocarbons selectively absorb radiation.

BRIEF DESCRIPTION OF THE DRAWINGS

FIG. 1 is a schematic depiction of the laser beam transmitter.

FIG. 2 is a cross-sectional schematic view of the transmission and receiving system.

DETAILED DESCRIPTION OF THE INVENTION

Referring now to FIG. 1, the laser beam transmitter 2 is schematically shown comprising a first $CO_2$ laser source 10 and a second $CO_2$ laser source 20. Laser sources 10 and 20 comprise mini-$CO_2$ transversely excited atmospheric (mini-TEA) lasers such as, for example, a grating tuned model T250 laser available from Marconi Avionics, Atlanta, Ga. One or both laser sources should be tunable to a particular wavelength using suitable tuning means such as a defraction grating.

Laser beam 12 from laser source 10 is passed through frequency doubling crystal 40 to summing crystal 50. Laser beam 22, emanating from laser source 20, is reflected by a mirror 30 and a polarization-discriminating beam combiner 32 to merge with frequency doubled laser beam 12' as it enters summing crystal 50. If both laser sources are pulsed simultaneously and summing crystal 50 is properly oriented (as is well known to those skilled in the art), the frequency of the laser beam 52 emerging from summing crystal 50 will be twice the frequency of beam 12 plus the frequency of beam 22. Since laser source 10 and laser source 20 are each capable of generating 80 different frequencies using normal isotopes, the combined frequencies capable of generation equals 6400. If other isotopes are used, this number may be multiplied to as high as 250,000. Furthermore, the effective frequency tripling of the system results in generation of wavelengths in the 3 micron region. This region is in a window of transmission with a low attenuation of the beam, thus providing a better signal to noise ratio at either the absorbed or unabsorbed frequency.

Doubling crystal 40 and summing crystal 50 are non-linear optical crystals which may be single crystals of a number of materials such as $CdGeAs_2$ or $AgGaS_2$, preferably $AgGaSe_2$ which has been calculated to yield a conversion efficiency of 7% when 2 cm. long crystals are used.

FIG. 2 illustrates a typical transmission and detection system which can be used in the practice of the invention. As shown, laser beam 52 from laser beam transmitter 2 is reflected by a 99% reflecting first mirror 60 to a second mirror 70 coaxially mounted in front of receiving telescope 100. Reflected beam 52 is then directed toward the target area as a beam coaxially with the receiving telescope. The beam passes through the atmosphere to be measured and then is reflected back to the receiving telescope via either man-made reflectors or, as will more commonly be the practice, via naturally occurring terrain or foliage.

The reflected beam 102 is intercepted by convergent lens mirror 110 which focuses reflected beam 102 onto mirror 120. Reflected beam 102 is then focused through relay lens 130 to a detector and receiver system 150 which, in the illustrated embodiment, consists of a thermoelectrically cooled indium arsenide infared radiation detector 152, amplifiers 153-155, and processing electronics comprising gated pulse stretcher 156 and pulse discriminator 157. In addition to the received signal preprocessing done at 150, data required by data processing system 200 includes information from power monitor system 160 and path length counter 170. Power monitor system 160, which has electronics similar to the receiver module 150, detects the small fraction of transmitted power passing through mirror 60. The detected power is used for normalizing the transmitted energy. Path length counter 170 provides range information.

The signal output from receiver 150, power monitor 160, and path lengths counter 170 is then processed by a single chip microprocessor 200 to determine the amount of absorption by the gas in question. This measurement is carried out by transmitting two wavelengths during a short time interval between transmissions, e.g. 50 microseconds apart, to ensure that they strike the same target, thereby calibrating target reflectivity which can vary spatially, and also eliminating atmospheric scintillation effects. One frequency is strongly absorbed by the gas to be detected, while the other frequency is weakly absorbed. The backscattered signal from the first frequency pulse is used to calibrate the gain of the system and reflectance of the topographic target. The ratio of backscattered signals between the two frequencies is a direct measure of the product of concentration and path length. Thus, because the technique involves the measurement of a differential rather than an absolute magnitude, it is self-calibrating.

The signals returned from the target are detected by receiver 150 and then processed by single chip microprocessor 200 which converts the analog signals to digital data and performs digital processing. The microprocessor calculates path-averaged concentration by first forming a ratio of the return signal at the two wavelengths, then takes the logarithm of the ratio, and finally multiplies this quantity by the inverse of the differential absorption coefficient times the range to the target. The target range varies considerably even for a given application and is automatically established by the time of flight of the laser pulses. The microprocessor may then output a continuous digital readout 210, a printed hard copy 220, or an audio alarm 230 for concentrations above a selected threshold depending up on the user's needs.

Similar detection systems and electronic processing can be substituted for that described. For example, in the article "Remote Measurement of Ethylene Using a $CO_2$ Differential-Absorption Lidar" previously cited, the authors describe the use of a HgCdTe detector for detection of the backscattered signals as well as the use of somewhat different signal processing apparatus. Reference is also hereby made to another publication in which some of present inventors participated entitled "Remote Measurement of HCl, $CH_4$, and $N_2O$ Using a Single-Ended Chemical-Laser Lidar System" by E. R. Murray, J. E. van der Laan, and J. G. Hawley in Applied Optics, volume 15 at page 3140 (Dec., 1976) which also used a HgCdTe detector.

It should be noted here that one of the advantages of the invention is the availability of thousands of different wavelengths from which to select. The large number of available wavelengths not only increases the number of different gases that can be measured, but it also allows optimization of the detection process. The optimization consists of finding the wavelength pairs for which the ratio of the differential absorption of the desired gas to the sum of the differential absorption of interfering gases and materials is maximum. For example, by use of a computer, the optimum pair of wavelengths for methane was found to be 2968.7639 $cm^{-1}$ and 2994.8511 $cm^{-1}$. In cases where no maximum exists, an interference problem usually can be overcome by making measurements at several wavelength pairs.

Thus, the practice of the invention grants the user much more flexibility to maximize the detection system both as to sensitivity for a particular gas as well as to the number of gases and combinations of gases that can be detected.

While the invention has been described in terms of specific preferred embodiments, it is recognized that minor modifications may be made therein which do not depart from the spirit of the invention which is to be limited only by the appended claims.

What is claimed is:

1. A system of detecting the presence of one or more gases in the atmosphere which comprises:
   a. a first laser source generating coherent light in the infrared portion of the spectrum;
   b. a second laser source generating coherent light in the infrared portion of the spectrum which may be at a different wavelength than said first laser source;
   c. means for doubling the frequency of said first laser source;
   d. summing means for adding the frequency of said second source to the doubled frequency said first source;
   e. means for changing the frequency of at least one of the laser sources;

f. means for transmitting a coherent light beam from said summing means through the atmosphere toward an object capable of reflecting light; and g. detecting means for receiving said reflected light and measuring the amount of light reflected by said object;

Whereby the amount and type of impurities in the atmosphere traversed by said beam of coherent light may be determined by transmitting a preselected wavelength not absorbed by such impurities and transmitting a second preselected wavelength known to be absorbed by such impurities and measuring the difference in amount of light received by said detecting means at the two frequencies.

2. The system of claim 1 wherein the laser sources are $CO_2$ lasers each capable of being tuned to 80 different frequencies and the resultant doubling of the frequency from one source added to the frequency from said other source provides a total of 6400 possible frequencies from which to select wavelengths respectively highly absorbed or slightly absorbed by a preselected gas.

3. The system of claim 2 wherein said means for doubling comprises frequency doubling crystal means.

4. The system of claim 3 wherein said summing means for adding the doubled frequency from said first laser source to the frequency of said second source comprises summing crystal means.

5. The system of claim 4 wherein both said crystal means are single crystals of the class having the formula $XYZ_2$ wherein X is selected from the class consisting of group IA and IB elements, Y is selected from the class consisting of group IIIA and group IVA elements, and Z is selected from the class consisting of group VA and VIA elements.

6. The system of claim 5 wherein the frequency doubling and the summing crystal means are single crystals of $AgGaSe_2$.

7. The system of claim 5 wherein the frequency doubling and the summing crystal means are single crystals of $AgGaS_2$.

8. The system of claim 5 wherein the laser beam transmission means comprise mirrors positioned to transmit the laser beam coaxial to the detecting means for receiving the reflected beam back from the reflecting object.

9. An improved system for the detection of one or more preselected gases in the atmosphere which comprises:

a. $CO_2$ laser beam means comprising:
 (1) a first $CO_2$ laser source;
 (2) a second $CO_2$ laser source;
 (3) crystal means for doubling the frequency of one of said laser sources;

b. means for transmitting said $CO_2$ laser means toward a target through the atmosphere which may contain gases which selectably absorb said laser beam at a preselected frequency; and c. means for detecting a reflected signal back from said target including means for determining signal strength;

whereby the presence or absence of a preselected gas may be ascertained using a laser beam at a preselected frequency highly absorbable by the preselected gas and at another frequency not highly absorbed to determine the presence of the gas based on differences in signal strength of the reflected beams at the two frequencies.

10. An improved method for detecting the presence of one or more preselected gases in the atmosphere which comprises:

a. generating a laser beam from a first laser beam source having a frequency in the infrared spectrum;

b. doubling the frequency of said laser beam;

c. generating a laser beam from a second laser beam source having a frequency in the infrared spectrum;

d. adding the doubled frequency from one of said laser beams to the frequency of the other laser beam to obtain a laser beam at a third frequency;

e. tuning at least one of said laser beams so that the third frequency produced by doubling one of the beam frequencies and adding it to the other frequency is a preselected frequency highly absorbed by said preselected gas;

f. transmitting said highly absorbable third frequency laser beam through the atmosphere toward a reflecting target;

g. detecting the reflected beam;

h. retuning at least one of said lasers so that the resultant third frequency laser beam is not highly absorbed by said preselected gas;

i. transmitting said resultant low absorption third frequency laser beam toward the same target;

j. detecting the reflected signal from said low absorption laser beam; and k. comparing the strength of the reflected highly absorbable laser beam with the reflected low absorption second laser beam to determine the amount of absorption of said first beam to thereby determine the presence or absence of said preselected gas in the atmosphere.

* * * * *